United States Patent [19]
Warner

[11] Patent Number: 5,650,329
[45] Date of Patent: Jul. 22, 1997

[54] ACID INDICATORS

[75] Inventor: Claude L. Warner, Chesterfield, Mo.

[73] Assignee: AWC, Inc., Chesterfield, Mo.

[21] Appl. No.: 480,506

[22] Filed: Jun. 7, 1995

Related U.S. Application Data

[63] Continuation of Ser. No. 71,700, Jun. 4, 1993, abandoned, which is a continuation-in-part of Ser. No. 572,057, Aug. 23, 1990, abandoned.

[51] Int. Cl.$^6$ .................................................. G01N 31/02
[52] U.S. Cl. .......................... 436/101; 436/163; 422/57; 422/58
[58] Field of Search ................. 422/56–58; 436/163, 436/101; 252/586

[56] References Cited

U.S. PATENT DOCUMENTS

| | | | |
|---|---|---|---|
| 2,823,984 | 2/1958 | Mavrodineau | 23/232 |
| 3,634,131 | 1/1972 | Foster | 427/353 |
| 3,912,844 | 10/1975 | Endo et al. | 428/500 |
| 4,910,803 | 3/1990 | Cukier | 422/58 |
| 4,999,306 | 3/1991 | Yafuso et al. | 436/68 |
| 5,094,955 | 3/1992 | Calandra et al. | 435/291 |

OTHER PUBLICATIONS

The Merck Index, The Tenth ed. 1983.

*Primary Examiner*—Lyle A. Alexander
*Attorney, Agent, or Firm*—Edward H. Renner

[57] ABSTRACT

Safety apparel for use in harardous environments has an indicating material incorporated in the surface of the apparel. On exposure to hazardous materials, such as acids and bases, the surface changes color to indicate exposure and provide a warning. Further, a material and method is provided to treat surfaces to indicate exposure to hazardous materials. The treated surfaces may exhibit reversibility effective to indicate exposure over repetitive cycles.

23 Claims, 1 Drawing Sheet

ACID INDICATORS

BACKGROUND OF THE INVENTION

This is a continuation of application Ser. No. 08/071,700 filed on Jun. 4, 1993 now abandoned which is a continuation-in-part of U.S. patent application Ser. No. 07/572,057 filed Aug. 23, 1990 now abandoned.

This invention relates to materials denoting the presence of hazardous substances to which industrial workers may be subjected by exposure or by spillage.

I am aware of the following U.S. patents, the disclosures of which are incorporated by reference herein:

| | |
|---|---|
| 2,823,984 | 4,328,181 |
| 4,094,642 | 4,731,333 |
| 4,205,043 | 4,795,611 |

With greater attention being directed to effects of exposure to hazardous substances, it is becoming increasingly important to monitor personal exposure to strong acids and bases, as known in the art, as well as other hazardous acids and bases. This is particularly true in and around chemical plants and factories emitting chemicals as adjuncts or byproducts of their operations.

One approach to monitoring personal exposure to hazardous materials has been the use of chemical indicators. In U.S. Pat. No. 4,205,043 a badge is provided for fire fighters for determining their exposure to toxic gases. Their badges consist of a plastic strip carrying filter paper discs, each impregnated with a predetermined concentration of an indicator chemical. The respective indicator discs change color in response to dosage levels of the chemical, such as HCN, $H_2S$, etc., to which test paper is sensitive.

In U.S. Pat. No. 4,328,181, an indicator material for the quantitative detection of low concentrations of selected hazardous materials is in the form of a pigmented porous coating. The pigment contains a chemical which reacts with the particular hazardous substance to give a visually resolvable color change.

U.S. Pat. No. 2,823,984 describes a fluoride ion detector for such compounds as HF, $SiF_4$, $H_2SiF_6$ and the like. An indicator is used having an absorbing surface impregnated with a zirconium or thorium nitrate and a dye that forms a lake with the nitrate. After exposure the indicator is developed in an acid solution to bring out the color changes.

Chemical safety rules now generally include, in addition to apparel such as goggles, gloves, coats, headgear and boots, some sort of atmospheric testing equipment, either test sets, or chemical indicators on an absorbent paper such as the badges of U.S. Pat. No. 4,205,043.

The prior art indicators are suggested for use on absorbing materials, their conditions of use being so critical and so specific that other detection materials are not obvious therefrom. Thus in U.S. Pat. No. 2,823,984 the indicator is immersed in an acid to develop the color change. More important, the problem of incorporating the indicator in a medium other than an absorbent remains to be solved.

Herein a material for detecting environmental hazardous substances is provided for use by workers who might be exposed to many strong acids such as sulfuric acid, hydrochloric acid, and hazardous acids, such as, hydrofluoric acid, and to strong and other hazardous alkalies, such as lime and caustic soda. There is a need for quickly detecting the presence of acids and bases in manufacturing plants, chemical transportation, storage and handling industries, chemical laboratories and research facilities to minimize injury by beginning decontamination as soon as contact is observed. There is also a need for detection means, beyond those prior art indicators described, to minimize injury by beginning decontamination when contact is observed. Such means are provided herein.

SUMMARY OF THE INVENTION

We have found that certain dyes responsive to strong and other hazardous acids and strong and other hazardous bases can be integrated with safety apparel so that the apparel itself becomes the hazardous substance indicator. This is particularly important in semiconductor and circuit board manufacturing and other etching plants or HF manufacturing plants where exposure to hydrofluoric acid, and many other substances such as strong acids and bases, is possible. The hazardous nature of hydrofluoric acid creates a need for such extraordinary precautions.

Safety apparel and equipment is thus provided which is adapted to caution a wearer of such apparel of contact with strong and other hazardous acids and bases. The safety apparel per se contains, integral therewith, a tautomeric dye. This dye is capable of changing from a tautomer of one color to a tautomer of a different color in response to environmental acid-base contact. An acid-base detecting material in the form of a coating composition is also contemplated which can be applied as a film section to clothing, or equipment, subject to exposure to strong and other hazardous acid or base atmospheres.

DETAILED DESCRIPTION OF THE INVENTION

Figure 1:
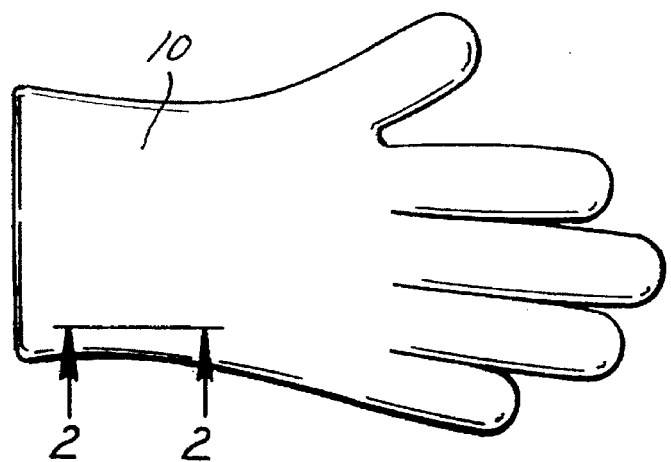
In FIG. 1 a glove treated by compositions of the invention is shown.

Heretofore for cautioning workers exposed to strong and other hazardous acids or bases some kind of portable device, such as an instrument or a badge with a known chemical indicator in an absorbent, has been used. These known warning devices have a number of limitations in actual use, particularly in the time before a warning is perceived. Herein, by the use of a suitable dye the indicator is made integral with the worker's protective gear. By integral it is intended that the protective clothing be impregnated with the dye, that the dye be incorporated in the article of clothing during manufacture, becoming a component thereof, or that a section of or portion of the apparel or equipment be coated with the dye material.

A strong and other hazardous acid-base detecting material is provided herein in the form of a coating composition which can be applied as a film section to the workers' protective gear or incorporated in the surface thereof. By acid-base is meant that the articles of clothing can be fabricated to respond to an acid environment or to a base environment depending upon working conditions where they are to be worn. Normally the clothing will be made sensitive to one of those conditions since plants generally create an acid or base atmosphere rather than both. Some specific coatings are destroyed by alkali if acid indicators, or, alkali if acid indicators also give a color change.

However, safety equipment responsive to environments which are acidic, basic, or both, may be produced by this invention.

The coating composition contains a dye which on exposure to strong and other hazardous acid-base atmospheres is capable of undergoing a color change on contact with the strong acid-base atmosphere. The dyes are believed to be tautomers whose tautomeric forms change, for example, color in response to acid-base solutions or vapors or liquid concentrations of less than 0.15 percent in moisture. In other words they also respond to gaseous or moist vapor atmospheres, and of course to spillage. Such coating compositions desirably will be solvent solutions, aqueous emulsions, plastisols and other coating compositions forming discontinuous films containing the dyes. Conventional solvents, such as acetone, methanol, ethanol, isopropyl alcohol, water, and the like, may be used. Resins forming continuous films may encapsulate the dye so that the strong or other hazardous acid or base will not contact the dye to effect the color change. Suitable resins include conventional vinyl, latex, acrylic, acetate, phenolic, epoxy, polyethylene, and polypropylene polymers and copolymers and equivalent polymers. These materials may be solubilized, plasticized, modified and applied, as known in the art. However, the proportion of resin to dye, while not critical, should not be so great as to fully encapsulate the dye. It has also been found, because of the adherent nature of dyes, the dye in solution can be employed as a coating composition. Normally in the case of rubberized boots, aprons, gloves, goggles and hard hats and other articles of clothing it will be desirable to coat a visible portion of that article of clothing. If the clothing is fabric, such as felt, paper or textile, it can be impregnated or coated with the dye. Dyes can also be made components of clothing, such as clean room attire, during manufacture. For example, certain paper products and rubber composition will readily accept the dyes and respond appropriately. The effectiveness of the invention can, perhaps, best be demonstrated by specific examples, by the application of the compositions to various articles of clothing, and by a specific illustration—that in the accompanying drawings. It should be noted that other surfaces, in addition to articles of clothing, may be coated by the materials and methods disclosed herein. For example, process equipment, piping, flanges and tanks may have all or a portion of their surfaces coated.

Specific examples will now be given to illustrate these considerations.

EXAMPLE 1

To obtain a dye solution about 50 mg of Victoria Blue B dye (Aldrich Catalog No. 19,969-9, Basic Blue 26) was added to 100 ml water and heated at 120° F. until completely dissolved. This heated solution was applied to surface 12 of latex gloves 10 such as that shown in FIG. 1. The blue dye remained on the surface on drying. When the gloves were exposed to liquid or gaseous HF the blue color immediately changed to light yellow brown. When rinsed with tap water, the blue color returned.

EXAMPLE 2

About ten mg of Victoria Blue R dye (Aldrich Catalog No. 23,417-6, Basic Blue 11) was added and dissolved in 100 ml isopropyl alcohol at room temperature until a clear solution was obtained. This solution was applied to rubber boots and the blue dye remained on the surface on drying. When the boots were exposed to liquid or gaseous HF the blue color immediately changed to light yellow brown. When rinsed with tap water, the blue color returned.

EXAMPLE 3

Figure 2:
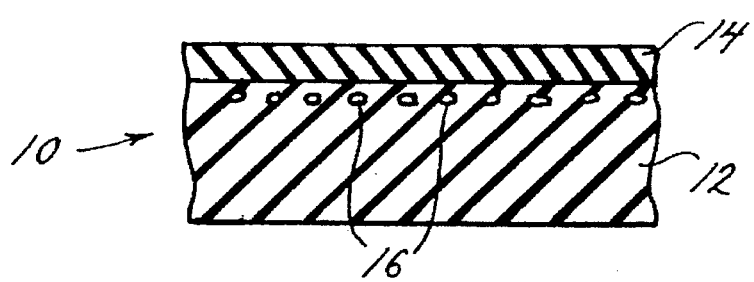
FIG. 2 is a cross-section through 2—2 of FIG. 1.

Example 2 was repeated using acetone in place of isopropyl alcohol. The resulting coating when applied to a latex glove 10 performed as described for Example 2. FIG. 2 shows this dye coating 14. Dye particles (16) have also penetrated into the surface 12 of glove 10.

EXAMPLE 4

Figure 3:
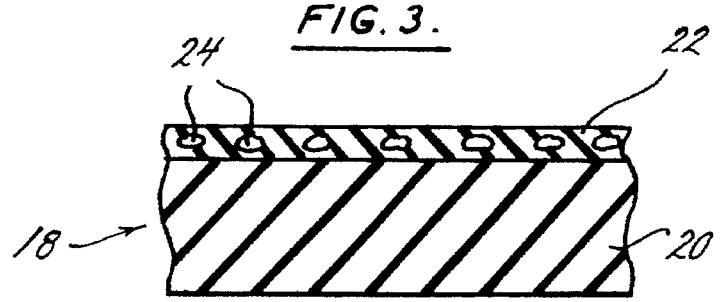
In FIG. 3, in cross-section, an additional embodiment is shown.

A latex indicator coating was prepared by combining at room temperature about 20 parts by weight of an over the counter clear urethane acrylic latex coating (Benjamin Moore Company, Code No. 415-00); about 50 parts water; 30 parts methanol; and three parts of Victoria Blue R dye. When applied to vulcanized rubber boots (18), and dried, the surface 20 had a latex coating 22 which appeared as in FIG. 3, with dye particles (24) suspended therein. Exposure to gaseous and liquid HF, was immediately discernible as in Example 2. However, the color was not as readily restored by a water wash.

EXAMPLE 5

About 50 mg Victoria Blue B dye was added and dissolved in 100 ml acetone until a complete solution was obtained. When this solution was applied to a rubberized jacket the blue dye remained on the surface on drying. When the jacket was exposed to liquid or gaseous HF the blue color changed to light yellow-brown. When rinsed with tap water, the blue color returned.

EXAMPLE 6

Alizarin dye (Aldrich catalog no. 12377-7, Mordant Red 11) was added and dissolved in methanol until a near saturated solution was obtained (approximately 1 mg/ml). When this solution was applied to clean room protective trousers the brownish red dye remained on the surface on drying. When the trousers were exposed to dilute 20% sodium hydroxide the brownish red color changed to bright purple. Equivalent results were obtained with ammonium hydroxide (household ammonia). A water rinse returns the garment back to the original brownish red color. This effect may be repeated, for example 2 to 3 cycles of exposure may be indicated. This system should be used only where human contact with the dye can be minimized, since alizarins have been implicated as potential carcinogens.

EXAMPLE 7

Alizarin was dissolved in isopropyl alcohol (0.175 grams per 100/ml.) and the solution was used to stain a white clean room garment light yellow with a brownish tint. In contact with sodium hydroxide the garment turned bright purple. The same color change occurred with ammonium hydroxide. The consideration concerning use, discussed in Example 6, should be followed.

EXAMPLE 8

Alzarin Red S Monohydrate (Aldrich Catalog No. 11,996-2 Mordant Red 3) was dissolved (about 1 mg/ml) in:
1. isopropyl alcohol,
2. acetone, and
3. water.

The solutions were coated on latex gloves and vinyl gloves to give a yellow-reddish brown color. The treated gloves turn purple when dilute (20%) sodium hydroxide or ammonium hydroxide is applied to the coated surface. The gloves responds to HF gas by turning white and finally bright yellow. The above solution was also applied to clean room garments, giving a bright yellow-brown color that instantly goes to bright purple in the presence of the two bases mentioned above. Acid such as 5% acetic, causes rapid chemical distruction, with yellow-white color. The consideration concerning use, discussed in Example 6, should be followed.

EXAMPLE 9

To obtain a dye solution about 5 mg of Pylachrome yellow dye (Pylan Products Co., Inc., Garden City, N.Y.) (Pylachrome Yellow LX-1913A) was added to 100 ml acetone and heated stirred slightly until completely dissolved. This solution was applied to the surface of 12 latex gloves 10 such as shown in FIG. 1. The bright yellow dye remained on the surface on drying. When the gloves were exposed to the listed acids the bright yellow color immediately changed to bright raspberry red. When rinsed with warm tap water, the bright yellow color returned. (Except when exposed to $H_2SO_4$ the red color may persist.)

EXAMPLE 10

About ten mg of Pylachrome yellow was added and dissolved in 100 ml methanol and acetone (30/70 by volume) at room temperature until a clear solution was obtained. This solution was applied to latex gloves and the bright yellow dye remained on the surface on drying. When the gloves were exposed to the listed acids the bright yellow color immediately changed to bright raspberry red. When rinsed with warm tap water, the original color returned. The sulfuric acid causes the red color to be more persistant.

EXAMPLE 11

A flexible, sprayable aerosol indicator coating was prepared by combining at room temperature the vehicle described in Example 15 and 1% by weight Pylachrome yellow dye. When applied to vulcanized rubber boots 18 from an aerosol can, and dried, the surface 20 had a flexible coating 22 which appeared as in FIG. 3, with dye particles (24) suspended therein. Exposure to gaseous and liquid acids was immediately discernible as in Example 10. However, the color is not as readily restored by a water wash, particularly on exposure to $H_2SO_4$.

EXAMPLE 12

A flexible, sprayable aerosol blue indicator coating about 1% by weight of Victoria Pure Blue BO Basic dye (Pylam Products #24550) was prepared substantially as described in Example 15 and coated, as described on boots. When exposed to liquid or gaseous acids the blue color changed to light yellow. When rinsed with tap water, the blue color generally returned. However, exposure to $H_2SO_4$ destroys the dye and resin and creates a clear spot on the surface.

The vehicle was prepared from:

| | Parts By Weight |
| --- | --- |
| acetone | 20 |
| propane | 20 |
| toluene | 5 |
| 2-butoxyethanol | 5 |

-continued

| | Parts By Weight |
| --- | --- |
| N-butane | 10 |
| acrylic resin (Rohm & Haas ACRYLOID (TM) B-72) | 5 |
| barium sulphate | 35 |
| 2-pentanone | 10 |
| propylene glycol methyl ether acetate | 10 |
| plasticizer | 2 |

EXAMPLE 13

The coating material of Example 12 was applied to the exterior surfaces of pipe fittings in an HF transport line, including flanges which were known to be leaking. The coating turned light yellow, which is very apparent, even if the observer is color blind, at the flanges where HF gas was leaking through the flange seal and provided a ready indicator for the areas where leaking was occurring. The flanges were tightened to eliminate the leaks and the coating was flushed with water. The blue color returned to the coating when washed and the dye coating was restored to a condition suitable to detect subsequent leaks. This coating will deteriorate (apparent as a slate gray color) on long exposure to direct sunlight, however, it is readily reapplied by spray coating and again effectively warns of leaks.

EXAMPLE 14

To obtain a dye solution about 1 part per volume of metanil yellow dye (Pylan Products Co., Inc., Garden City, N.Y.) (Metanil Yellow, acid yellow 36) was added to 1500 parts by volume of tap water at about 120° F. and agitated slightly until completely dissolved. This solution was applied by pump aerosol spray to test surface. The bright yellow dye remained on the surface on drying. When the surfaces were exposed to the listed acids the bright yellow color immediately changed to a rich purple. The treated surface was flushed with water and retested with spray to confirm that acid had been removed.

EXAMPLE 15

About one part by weight of Pylachrome yellow (Pylan LX 1913A) was added and dissolved in 440 parts by weight of solvent and resin preparation shown herein, and mixed until a clear solution was obtained. This solution was charged to a pressure aerosol can and sprayed on a test surface. The surface was exposed to the listed acids and the bright yellow color immediately changed to bright raspberry red. When rinsed with warm tap water, the original color returned. The sulfuric acid causes the red color to be more persistant. This coating provided a flexible painted surface which provides persistent indicating properties, as much as eighteen months or more, especially in environments which are protected from strong UV and direct sunlight. In any case, the effect may persist for several months. The material is readily recoated to renew the effect.

| | Parts By Weight |
| --- | --- |
| acetone | 30 |
| propane | 20 |
| toluene | 5 |
| butyl benzyl phthalate (plasticizer) | 5 |
| 2-butoxyethanol | 5 |
| N-butane | 10 |
| acrylic resin (Rohm & Haas ACRYLOID (TM) B-72) | 5 |

The material described in Example 15 was spray coated in an exhaust hood where hydrofluoric acid is commonly used.

The coating exhibits a strong color change to red in the presence of HF fumes, and readily indicates the presence of an open HF container in the hood. The color persists even when the hood fan is operating to exhaust the hood and remains after the container is removed until the air currents have purged the coated surface and the color changes back to yellow. The indicating property of the surface persists through many cycles.

As indicated hereinbefore, acid and base properties of the environment tend to bring about color changes in certain dyes. Such dyes are tautomers which in equilibrium in their basic form are one color, and which in their acidic state are another color. The acid-base reaction, then converts a tautomer of one color to a tautomer of a different color. Thus an acid converts some tautomeric dyes to an acid form and the addition of a base converts other dyes to an alkaline tautomer of different color. The preferred dyes herein are the Victoria (diphenylnaphthylmethane) dyes, such as Victoria pure blue BO (basic blue 7, Aldrich catalog no. 23,098-7) and the like, which change color when exposed to strong acids, and the alizarin (anthraquinone) dyes, methyl orange and methyl red (monoazo) dyes which change color when exposed to strong bases. The metanil (yellow) dyes are in many instances especially preferred in aqueous solutions. The Pylachrome yellow dyes work especially well in resin vehicle systems. Generally, small amounts of dye per unit vehicle are effective to provide suitable coatings, since the color strength of the dyes is strong. The particular proportions of dye are not critical, but high proportions of dye are not necessary and only add to the cost of the coating composition.

It is understood that not all of these dyes respond to acids and bases in the same way. Thus some may respond only to acids in liquid form whereas others will respond to both the gaseous and liquid forms of acids or bases. However selection of the appropriate dye can be made based on the examples given herein. It is also to be understood that the vehicle employed on the application of the dye to the protective clothing will depend upon the particular piece of safety apparel to which it is applied. Since the article of protective clothing, in effect, is the substrate, and the vehicle must bond to that substrate. Hence some judgment must be exercised. Thus a water based dye does not adhere to vinyl boots and gloves, but does adhere to rubber products. In the case of vinyl protective articles of apparel a latex-based dye coating composition may be used, but a resin based aerosol is especially preferred, such as Example 15. A vinyl substrate treated with isopropyl alcohol as a solvent carrier may have a weak response to HF gas, but will respond strongly to liquid exposure, for example.

It has been emphasized that the dye is applied to the apparel by coating a section of the clothing with a film of dye-containing coating, by impregnating the clothing by spraying or dipping or by introduction of the dye during the manufacturing process. Again selection of the method of application will depend upon the particular garment. In addition both acid and base responsive dyes can be applied to the clothing if conditions warrant such application. Such selections and applications will be obvious to those in the field, given the teachings of this invention. Such variations and modifications are deemed to be within the scope of the invention.

It will be appreciated by those skilled in the art that many variations of the embodiments disclosed herein may be made without departing from the spirit of the invention. The invention is not to be limited to the embodiments disclosed herein for purposes of illustration, but only to the claims appended hereto and their equivalents.

We claim:

1. A hazardous acid-base detecting material, the material comprising a coating composition which can be applied as a film section to worker's protective gear subject to exposure to hazardous acid-base atmospheres, the coating composition containing a vehicle and a dye effective to undergo, when the film section on the protective gear is dried, a color change on being contacted by the hazardous acid-base atmosphere, the dye being a tautomer whose tautomeric forms are effective to an acid-base atmosphere containing less than 0.15 percent moisture, and the vehicle being selected from the group consisting of vinyl, latex, acrylic, acetate, phenolic, epoxy, polyethylene, and polypropylene polymers and copolymers.

2. A hazardous acid-base detecting material, the material comprising a coating composition which can be applied as a film section to surfaces subject to exposure to hazardous acid-base atmospheres, the coating composition containing a vehicle and a dye effective to undergo a color change, when the film section on the surfaces is dried, on being contacted by a hazardous acid-base atmosphere, the dye being a tautomer whose tautomeric forms are effective to change color, in use, in response to acid-base vapors containing less than 0.15 percent moisture, the dye being selected from the group consisting of Victoria Blue dyes, metanil yellow, alizarin dyes and Pylachrome yellow, and the vehicle being selected from the group consisting of vinyl, latex, acrylic, acetate, phenolic, epoxy, polyethylene, and polypropylene polymers and copolymers.

3. The material of claim 2 wherein the dye is Pylachrome yellow and the vehicle is an acrylic resin effective in the dried film to permit a color change inducing contact in a hazardous acid-base atmosphere.

4. The coating composition of claim 2 wherein the vehicle is a solvent for the dye.

5. The coating composition of claim 4 wherein the vehicle is an alcohol, the dye is alizarin yellow and the dye is responsive in an atmosphere which contains sodium hydroxide.

6. The coating composition of claim 4 wherein the vehicle is an alcohol, the dye is alizarin yellow responsive to an atmosphere containing sodium hydroxide.

7. The coating composition of claim 2 wherein the vehicle is a latex emulsion.

8. The coating of claim 7 wherein the dye is Victoria Blue B responsive to an atmosphere containing HF gas.

9. The coating of claim 7 wherein the dye is Victoria Blue B and the dye is responsive in an atmosphere which contains HF gas.

10. The coating composition of claim 9 wherein the vehicle is water.

11. The coating composition of claim 7 wherein the vehicle is a latex base clear acrylic coating.

12. The coating composition of claim 11 wherein the dye is alizarin and the dye is responsive in an atmosphere which contains HF gas.

13. The coating composition of claim 11 wherein the dye is alizarin responsive to an atmosphere containing HF gas.

14. The method of testing for the presence of hazardous acids and bases comprising applying to a surface to be tested a hazardous acid or base detecting material in the form of a coating composition, the coating composition being applied as a film to the surface, subjecting the surface to exposure to a hazardous acid or base containing environment, the coating composition containing a dye effective to undergo a color change, in use, when the film section is dried, on being contacted by the hazardous acid or base containing environment, the dye being a tautomer whose tautomeric forms are effective to change color in response to an acid or base containing gas or vapor having less than 0.15% moisture content, the dye being selected from the group consisting of Victoria Blue dyes, metanil yellow, alizarin dyes and Pylachrome yellow, the vehicle being selected from the group consisting of vinyl, latex, acrylic, acetate, phenolic, epoxy, polyethylene, and polypropylene polymers and copolymers.

15. The method of claim 14 wherein the dye is Victoria Blue B responsive to an atmosphere containing HF gas.

16. The method claim 14 wherein the vehicle is an alcohol, the dye is alizarin yellow responsive to an atmosphere containing sodium hydroxide.

17. The method of claim 14 wherein the dye is alizarin responsive to an atmosphere containing HF gas.

18. The method of claim 14 wherein the dye is metanil yellow.

19. The method of claim 14 wherein the coating includes an acrylic resin effective to form a film on the surface, the film being effective to permit a color change inducing contact between the hazardous acids or bases and the dye.

20. The method of claim 14 wherein the dye is Pylachrome yellow.

21. The method of claim 14 wherein the dye is Victoria Blue R.

22. The method of claim 14 wherein the dye is Victoria Blue B.

23. The method of claim 14 wherein the vehicle is an acrylic resin substantially porous to the hazardous acid or base and being effective to permit a color change inducing contact between the hazardous acids or bases and the dye.

* * * * *